US005550294A

United States Patent [19]

Whitman

[11] Patent Number: 5,550,294

[45] Date of Patent: Aug. 27, 1996

[54] METHOD OF INCREASING HYDROGENATION RATE OF AROMATIC AMINES

[75] Inventor: Peter J. Whitman, Hamden, Conn.

[73] Assignee: Olin Corporation, Cheshire, Conn.

[21] Appl. No.: 307,215

[22] Filed: Sep. 16, 1994

Related U.S. Application Data

[63] Continuation-in-part of Ser. No. 831,712, Feb. 5, 1992, abandoned.

[51] Int. Cl.[6] .................... C07C 209/72

[52] U.S. Cl. .................... 564/451; 564/450; 564/452

[58] Field of Search .................... 564/451, 450, 564/457, 462, 461

[56] References Cited

U.S. PATENT DOCUMENTS

| | | | |
|---|---|---|---|
| 2,551,028 | 6/1950 | Whitman | 260/563 |
| 2,606,924 | 8/1952 | Whitman | 260/563 |
| 2,606,925 | 8/1952 | Whitman | 260/563 |
| 2,606,928 | 8/1952 | Barkdell et al. | 260/563 |
| 3,155,724 | 11/1964 | Arthur | 260/563 |
| 3,347,917 | 10/1967 | Arthur | 260/563 |
| 3,591,635 | 7/1971 | Farrissey et al. | 260/563 B |
| 3,636,108 | 1/1972 | Brake | 260/563 |
| 3,644,522 | 2/1972 | Brake et al. | 260/563 |
| 3,679,746 | 7/1972 | Brake | 260/563 R |
| 3,697,449 | 10/1972 | Brake | 252/474 |
| 3,711,550 | 1/1973 | Brake | 260/563 |
| 3,766,272 | 10/1973 | Brake | 260/563 |
| 3,856,862 | 12/1974 | Chung et al. | 260/563 B |
| 3,959,374 | 5/1976 | Brennan et al. | 260/563 B |
| 4,394,522 | 7/1983 | Allen | 564/451 |
| 4,394,523 | 7/1983 | Allen | 564/451 |
| 4,448,995 | 5/1984 | Allen | 564/451 |
| 4,754,070 | 6/1988 | Casey et al. | 564/451 |
| 4,946,998 | 8/1990 | Casey et al. | 564/451 |
| 4,960,941 | 10/1990 | Vedage et al. | 564/450 |

FOREIGN PATENT DOCUMENTS

| | | |
|---|---|---|
| 1122609 | 8/1968 | United Kingdom . |

*Primary Examiner*—Brian M. Burn
*Attorney, Agent, or Firm*—Dale L. Carlson

[57] ABSTRACT

A process for increasing the rate of catalytic hydrogenation of aromatic amines by reacting aromatic amines with hydrogen in the presence of a noble metal catalyst, a water miscible organic solvent, lithium hydroxide catalyst promoter, and water in an effective amount to increase the rate of the hydrogenation reaction without an appreciable increase in total amounts of by-products.

12 Claims, No Drawings

METHOD OF INCREASING HYDROGENATION RATE OF AROMATIC AMINES

This application is a continuation-in-part application of U.S. Ser. No. 07/831,712 filed Feb. 5, 1992, now abandoned.

FIELD OF THE INVENTION

This invention relates to a process for increasing the reaction rate in the catalytic hydrogenation of aromatic amines to produce their hydrogenated counterparts.

BACKGROUND OF THE INVENTION

A substantial body of literature exists with respect to the catalytic hydrogenation of aromatic amines to prepare the corresponding cycloaliphatic amines. Illustrative of this type of reaction is the hydrogenation of methylenedianiline [4,4'-diaminodiphenylmethane, MDA] to the corresponding cycloaliphatic amine, bis (4-aminocyclohexyl)methane [$H_{12}$MDA, PACM].

The hydrogenation follows a step-wise reaction sequence, giving first the half hydrogenated cis and trans isomers of p-(4-aminocyclohexylmethyl)aniline, [4-(p-aminobenzyl)aminocyclohexane, $H_6$MDA], then reacting further to yield the three bis(4-aminocyclohexyl)methane isomers (cis, cis; cis, trans; and trans, trans) represented by the formulas and reactions as follows:

HYDROGENATION OF METHYLENEDIANILINE (I)

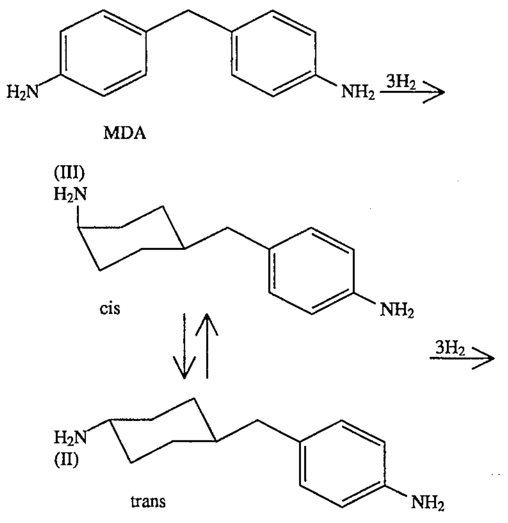

MDA (III)

cis (II)

trans $H_6$MDA

-continued

HYDROGENATION OF METHYLENEDIANILINE (VI)

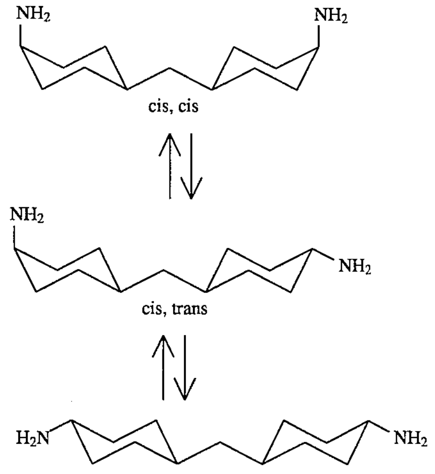

cis, cis (V)

cis, trans (IV)

trans, trans $H_{12}$MDA

Some of the early hydrogenation work to produce bis(4-aminocyclohexyl)methanes was done by Whitman and Barkdoll, et al and their work is set forth in a series of U.S. Pat. Nos. 2,511,028, 2,606,924, 2,606,925 and 2,606,928. Basically the processes described in these patents involve the hydrogenation of methylenedianiline at pressures in excess of 200 psig, preferably in excess of 1,000 psig at temperatures within a range of 80° to 275° C. The hydrogenation is carried out under liquid phase conditions and an inert organic solvent is used. Most of the references utilize a noble metal catalyst such as ruthenium, rhodium, iridium, or mixtures of any of these or with platinum or palladium, either as the hydroxide, oxide, or the metal itself on an inert support. Examples of ruthenium catalysts utilized for the hydrogenation process include ruthenium oxides, such as ruthenium sesquioxide and ruthenium dioxide; ruthenium hydroxide; and ruthenium salts.

The isomeric cycloaliphatic diamines are useful in the preparation of the corresponding aliphatic diisocyanates suitable for forming light stable urethane coatings and lacquers. In earlier experiments involving the hydrogenation of aniline, it was shown that addition of ammonia not only suppresses by-product formation mainly from hydrogenolysis and condensation reactions, but also poisons the catalyst. However, addition of lithium hydroxide and sometimes sodium hydroxide suppresses the hydrogenolysis without the detrimental poisoning of the catalyst. A similar phenomenon has been reported with the hydrogenation of methylenedianiline using lithium hydroxide, and to a lesser extent, with other alkali or alkaline earth hydroxides or alkoxides. Common by-products formed during the hydrogenation of methylenedianiline include the hydrogenolysis products 4-aminodicyclohexylmethane and 4-aminocyclohexylcyclohexenylmethane, the hydrolysis product 4-amino-4'-hydroxydicyclohexylmethane, and higher boilers, mainly higher molecular weight secondary amine condensation products. All of these products exist as a number of isomers.

In the continued development of processes for manufacturing bis(4-aminocyclohexyl)methanes by hydrogenating methylenedianiline it was found that if the ruthenium was loaded upon a support and the support was alkali-moderated, the catalyst was much more active and catalytically effective in producing the desired hydrogenated bis(4-aminocyclohexyl) methane product. Alkali moderation was effected by contacting the catalyst with an alkali metal hydroxide or alkoxide; also, such alkali moderation of the catalyst could be effected prior to hydrogenation or in situ during the hydrogenation. Representative patents showing the utilization of alkali moderated ruthenium catalysts to hydrogenate methylenedianiline include U.S. Pat. Nos. 3,636,108, 3,644,522 and 3,697,449. Alkali metal and alkaline earth metal nitrates and sulfates have similarly been shown effective in U.S. Pat. No. 4,448,995 under high pressure (4000 psig) hydrogenation conditions.

U.S. Pat. No. 3,959,374 discloses a process for the preparation of bis(4-aminocyclohexyl)methane by pretreating a mixed methylenedianiline system with a nickel-containing hydrogenation catalyst prior to hydrogenation with ruthenium. The pretreatment was used to overcome low yields (52.4%) and long reaction time associated with nickel and cobalt catalysts. Ruthenium catalysts, although commonly used for hydrogenation, were not suited for hydrogenation of a feed containing impurities according to the teachings of the '374 patent, since impurities in the feed caused a rapid decline in activity and hydrogenation efficiency.

U.S. Pat. Nos. 3,347,917; 3,711,550; 3,679,746; 3,155,724; 3,766,272 and British Patent No. 1,122,609 disclose various isomerization and hydrogenation processes to produce bis(4-aminocyclohexyl)methane containing a high trans,trans-isomer content; i.e. an isomer content near equilibrium typically 50% trans,trans, 43% cis,trans and 7% cis,cis. Ruthenium catalysts were used to effect isomerization.

In U.S. Pat. Nos. 4,394,522 and 4,394,523, processes are disclosed for producing bis(4-aminocyclohexyl)methane by carrying out the hydrogenation of methylenedianiline in the presence of unsupported ruthenium dioxide at pressures of at least 2500 psig or in the presence of ruthenium on alumina under pressures of at least 500 psig and preferably from 1500 psig to 4000 psig in the presence of an aliphatic alcohol and ammonia. Other catalysts have been utilized for the hydrogenation of methylenedianiline and examples are shown in U.S. Pat. Nos. 3,591,635 and 3,856,862 which disclose the use of a rhodium component as a catalytic material and each require the use of an alcohol as a solvent. The rhodium is alkali moderated using ammonium hydroxide as a pretreatment or by carrying out the reaction in the presence of ammonia.

Although different organic solvents and mixtures have been used (generally ethers and alcohols), aqueous systems have generally not been utilized. U.S. Pat. No. 4,448,995 teaches that this reaction should be maintained in an anhydrous state or at least maintained so that water concentration is less than 0.5% by weight because failure to do so results in an increase in both the amount of alcohol by-products and higher molecular weight condensation products. In addition, the patent states that alkali nitrates and sulfates, especially those of lithium reduce by-products.

U.S. Pat. Nos. 4,960,491 and 4,754,070 disclose the hydrogenation of aromatic amines to their hydrogenated counterparts. In these patents, it is stated that "Although in some processes water can be used as a co-solvent, it is preferred that the system be in an anhydrous state or at least maintained so that the water concentration is less than 0.5 percent by weight. Water, when present in the system, tends to increase the amount of by-product alcohols and heavy condensation products during the hydrogenation process and tends to deactivate the catalyst system."

Representative supports for ruthenium catalysts for the hydrogenation of aromatic amines in aqueous alkaline media are disclosed in U.S. Pat. No. 3,697,449, including bauxite, periclase, zirconia, titania, and diatomaceous earth. The '449 patent discloses a series of hydrogenation reactions of methylenedianiline using a sodium hydroxide promoter while varying the amount of water employed in the reaction mixture, although disclosing no advantages associated with the use of water, and instead teaching that "excessive quantities" of water above about 5 weight percent causes unwanted by-product formation. More specifically, it is disclosed in the working examples of the '449 patent that increased water in the hydrogenation reaction mixture lowers the yield of product, and it is stated in claim 1 "that the maximum amount of water that can be present in the reaction medium is about 5 weight percent of said medium". Moreover, the '449 patent discloses, at column 1, lines 56–60 thereof, that the hydrogenation of aromatic amines in aqueous alkaline systems in the presence of more than about 5% water in the medium results in the formation of undesirable byproducts. The '449 patent also states that "if the basic alkali metal compound is added to the hydrogenation process as an aqueous slurry or solution, the amount of water added should be no more than about 5% by weight of the reaction mixture. Excessive quantities of water will normally result in the formation of undesirable by-products, including the corresponding hydroxy derivatives, deamination products, and polyamines."

In some comparisons, the presence of lithium hydroxide has been shown to actually result in an increase in the production of higher molecular weight products. (See U.S. Pat. No. 4,946,998.)

New processes for the hydrogenation of aromatic amines that provide a rapid rate of reaction without appreciable by-product production would be highly desired by the saturated cyclic amines manufacturing community. The present invention provides one such process.

SUMMARY OF THE INVENTION

In one aspect, the present invention relates to a process for the catalytic hydrogenation of an aromatic amine represented by the formula:

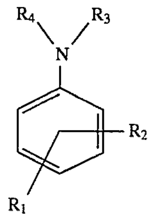

(VII)

in which:

$R_1$ is selected from the group consisting of H, an alkyl or cycloalkyl group having 1–6 carbon atoms, and $NH_2$;

$R_2$ is selected from the group consisting of H, an alkyl or cycloalkyl group having 1–6 carbon atoms, and

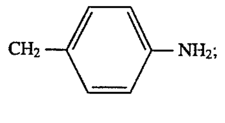

and $R_3$ and $R_4$ are selected from the group consisting of H, and an alkyl or cycloalkyl group having 1–6 carbon atoms;

which process comprises reacting a reaction mixture comprising said aromatic amine and hydrogen at a pressure of between about 500 and about 4000 psig in the presence of a noble metal catalyst, a lithium hydroxide catalyst promoter, and a water miscible organic solvent, said reaction mixture containing water in an amount of between 7% and 12% (preferably between 7% and 10%) by weight, based upon the weight of the reaction mixture.

In another aspect, the present invention relates to a composition useful for the catalytic hydrogenation of aromatic amines comprising:

(a) an aromatic amine, (b) a noble metal catalyst, (c) lithium hydroxide, as a catalyst promoter, (d) a water-miscible organic solvent containing water in an amount of between 7% and 12% by weight based upon the weight of the composition.

These and other aspects will become apparent upon reading the following detailed description of the invention.

DETAILED DESCRIPTION OF THE INVENTION

It has now been surprisingly found in accordance with the process of the present invention that the reaction rate of catalytic hydrogenation of aromatic amines is facilitated when lithium hydroxide is used as a promoter, in the presence of water in amounts of between 7% and 12% (preferably between 7% and 10%) by weight, based upon the weight of the reaction mixture, in the presence of a co-solvent. In addition, by-product formation is minimized, relative to analogous reactions using higher or lower water amounts outside of the above-specified broad range. This result is particularly surprising in view of the teachings of the above-discussed '449 patent to the effect that the amount of water in an aromatic amine hydrogenation reaction should not exceed about 5 weight percent in order to avoid undesirable by-product formation.

The present invention relates to a process for increasing the rate of conventional ring hydrogenation of aromatic amines to their hydrogenated counterparts and these aromatic amines are represented by the formula:

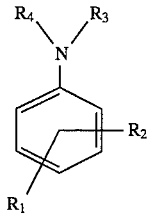

(VII)

in which $R_1$ is selected from the group consisting of H, an alkyl or cycloalkyl group having 1–6 carbon atoms, and $NH_2$;

$R_2$ is selected from the group consisting of H, an alkyl or cycloalkyl group having 1–6 carbon atoms, and

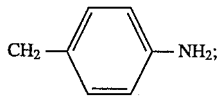

and $R_3$ and $R_4$ are selected from the group consisting of H, and an alkyl or cycloalkyl group having 1–6 carbon atoms.

By the practice of this invention, one is able to increase the rate of hydrogenation of aromatic amines to their hydrogenated counterparts without an appreciable increase in the total amounts of the by-products formed during reaction. The aromatic amines useful in the practice of the process can be bridged polynuclear or mononuclear aromatic amines. These can be substituted with various substituents such as an alkyl group or cycloalkyl group containing from 1–6 carbon atoms. Further, the amine group can be substituted with alkyl or cycloalkyl groups having 1–6 carbon atoms resulting in secondary and tertiary amine substituents. Examples of bridged aromatic amines include methylenedianiline ($R_1$ is H and $R_2$ is

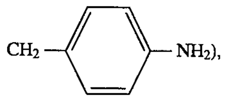

), bis (4-amino-2-methylphenyl)methane, toluidine, and alkyl or cycloalkyl secondary and tertiary amine derivatives of above aromatic amines. Examples of mononuclear aromatic amines include 2,4- and 2,6-toluenediamine, aniline, 1-methyl-3,5-diethyl-2,4- or 2,6-diaminobenzene (diethyltoluenediamine), diisopropyltoluenediamine, tert-butyl-2,4- or 2,6-toluenediamine, cyclopentyltoluenediamine, ortho-toluidine, ethyltoluidine, xylenediamine, mesitylenediamine, mono-isopropyltoluenediamine, phenylenediamine, and alkyl and cycloalkyl secondary and tertiary amine derivatives of the aromatic amines mentioned above.

As with conventional processes the hydrogenation process is carried out under liquid phase conditions being maintained typically by carrying out the hydrogenation in the presence of a solvent. Any solvent miscible with water at the reaction temperature and inert to the reaction conditions should be equally usable. Representative solvents suitable for practicing the invention include low molecular weight alcohols, such as methanol, ethanol, isopropyl alcohol, tert-butyl alcohol and methoxyethanol; and low molecular weight aliphatic and alicyclic hydrocarbon ethers, such as n-propyl ether, isopropyl ether, glyme, tetrahydrofuran, and dioxane. Isopropyl alcohol is preferred.

The amount of water employed in the reaction mixture depends on the following factors: organic solvent, starting aromatic amine, resulting corresponding hydrogenated amine counterpart, and temperature. Thus, the minimum water concentrations to be effective to increase the rate of the hydrogenation reaction should be in amounts greater than 7% by weight of the reaction medium. However, the maximum amount of water added depends on the amount and nature of organic solvent present. Carrying out the reaction in the presence of water without an organic solvent is deleterious, and balling of the catalyst was observed. Thus, as used in the specification and claims hereof, the term "effective amount" is intended to include any such amount. By way of illustration, an effective amount of the water is a range of from about 7% up to solubility limits of the starting product and/or the reaction product in the resultant mixed water-organic solvent, preferably from about 7% to about 12% and most preferably from about 7% to about 10% by weight of the reaction medium.

A noble metal catalyst such as ruthenium, rhodium, iridium, or mixtures of any of these or with platinum or palladium, either as the hydroxide, oxide or, the metal itself on an inert support may be utilized for the hydrogenation process. The catalysts used are supported upon an inert carrier and representative carriers include carbon; calcium carbonate; rare earth oxides such as cerium, praseodymium, or lanthanum; rare earth carbonates; alumina; barium sulfate; kieselguhr; pumice; titania; diatomaceous earth; and other alkaline earth compounds such as calcium sulfate, calcium oxide, barium oxide, and barium sulfate. Preferred support material is alumina. The preferred catalyst is ruthenium on alumina carrier ($Ru/Al_2O_3$). A 5% ruthenium on alumina loading is illustrative, but any percent loading can be utilized.

To maintain high activity of the catalyst system in the hydrogenation process, the noble metal component of the catalyst is lithium hydroxide moderated. Alkali moderation techniques to produce such a catalyst and/or catalyst system are well known and the techniques are disclosed in U.S. Pat. No. 3,636,108. Such techniques can be utilized for rhodium as well as ruthenium. Such alkali moderation involves the treatment of the catalyst and support material with an alkali metal hydroxide such as lithium, sodium or potassium hydroxide or alkali metal alkoxide such as lithium, sodium, or potassium methoxide or ethoxide in an amount to provide from 0.01% to 2% by weight based on the starting aromatic amine. Alkali moderation can be accomplished in situ during hydrogenation by including alkali metal hydroxide, or alkali metal alkoxide. The most effective promoter or moderator and the most preferred is lithium hydroxide. Unlike the other alkali and alkaline earth hydroxides, lithium hydroxide exists most commonly as the monohydrate $LiOH \cdot H_2O$ and thus a totally anhydrous system using lithium hydroxide is difficult to achieve. As used herein the term lithium hydroxide refers to either the monohydrate or the anhydrous material.

The temperature range of the reaction is 80°–240° C. In the case of methylenedianiline, the optimum temperature is dependent on the desired bis(4-aminocyclohexyl)methane isomer ratio. In order to achieve a 20% trans, trans content or less the lower end of the temperature range is desirable. To achieve a 48% trans,trans content, this reaction must take place in the midrange or above 170° C.

Pressures used in the reaction of the process of this invention range from about 500–4000 psig with the preferred range 700–3000 psig.

The concentration of starting aromatic amine in solution can vary from 10 to 95% (without solvent), preferably 50% to 90% are utilized.

The progress of the hydrogenation reaction is followed readily by observation of the amount of hydrogen taken up by the reaction mixture and the hydrogenation is terminated at the point at which the theoretical quantity of hydrogen has been absorbed. Following the hydrogenation, the catalyst is separated from the solution of reduced material. The following examples are presented to further illustrate the invention without any intention of being limited thereby. All parts and percentages are by weight unless otherwise specified except for percent yield which is mole percent.

EXAMPLE 1

Into a 600 ml Parr pressure reactor, the following were added: 100 g of methylenedianiline, 0.4 g of lithium hydroxide monohydrate, 20 g of isopropyl alcohol, 10 g of water, and 7 g of 5% ruthenium on alumina. The reactor was flushed with hydrogen and pressurized to about 850 psig. The reaction mixture was heated to 120° C. and stirred at about 1000 psig. Each time the hydrogen pressure decreased to about 950 psig due to uptake, the reactor was recharged to about 1050 psig with more hydrogen. Hydrogen uptake ceased at about 4.4 hours. After cooling and release of pressure, the reaction mixture was filtered, optionally through celite.

Several other hydrogenation reactions were carried out at 1000 psig and 116°–120° C. with various amounts of solvents and lithium hydroxide monohydrate. The results are shown below:

| | Reaction conditions | | | |
|---|---|---|---|---|
| Example No. | Time (hr.) | $LiOH.H_2O$ (g) | $IPA/H_2O$ (g/g) | Amt of $H_2O$ as % of Reaction Mixture |
| 1 | 4.4 | 0.4 | 20/10 | 73 |
| 2 | 5.9 | 0.4 | 10/10 | 72 |
| 3 | 6.3 | 0.4 | 20/5 | 32 |
| 4 | 7.8 | 0.4 | 20/0 | 0 |
| 5 | 7.7 | 0 | 20/0 | 0 |
| 6 | 5.5 | 0 | 20/10 | 7.8 |
| 7 | 3.5 | 0.4 | 0/10 | 8.5 |
| 8 | 7.8 | 0.4 | 10/20 | 14.6 |

| | Product Distribution | | | | | | |
|---|---|---|---|---|---|---|---|
| Example No. | bis(4-amino-cyclohexyl)-methane | p-(4-amino-cyclohexyl-methyl)aniline | 2,4'-diamino-dicyclohexyl-methane | mono-amines | hydroxy-amines | N-isopropyl-bis(4-amino-cyclohexyl)-methane | heavies |
| 1 | 96.7 | 0.1 | 1.7 | 1.2 | 0.3 | <0.1 | <0.1 |
| 2 | 95.1 | <0.1 | 1.7 | 1.4 | 0.7 | <0.1 | <0.1 |
| 3 | 96.1 | 0.3 | 1.7 | 1.1 | 1.7 | 0.1 | 0.1 |
| 4[1] | 62.5 | 30.0 | 1.2 | 1.0 | 0.3 | 0 | 0.1 |
| 5[1] | 48.8 | 22.3 | 0.5 | 18.4 | 4.0 | 0.1 | 4.0 |
| 6 | 67.2 | 0.1 | 1.0 | 14.0 | 11.0 | 0.1 | 5.8 |
| 7[2] | — | — | — | — | — | — | — |
| 8 | 57.5 | 40.0 | 1.6 | 2.2 | 3.1 | 0 | 0.8 |

The normalized trans, trans isomer content of the bis (4-aminocyclohexyl)methane in the reactions that approach completion is 20–24%.
[1]Many other peaks corresponding to intermediates are not listed here.
[2]This reaction stopped because very little $H_2$ uptake was observed. The catalyst balled up.

Thus, water unexpectedly increased the reaction rate. Experiments 4 and 5 which contain no water are slow. In the presence of water but the absence of lithium hydroxide, a good reaction rate is observed, but a large amount of by-product is formed. Carrying out the reaction without a water-miscible organic solvent (experiment 7) results in an even slower reaction.

Optimum results, a fast rate and a high yield of bis(4-aminocyclohexyl)methane, are obtained in the catalytic hydrogenation of methylenedianiline by utilizing >7% water, lithium hydroxide promoter, and a water-miscible solvent such as isopropyl alcohol. This combination was entirely unexpected.

Operable and preferred ranges of reaction conditions are presented in the following table:

TABLE 1

| | Range | |
|---|---|---|
| Variable | Operable | Preferred |
| Temperature | (1) | (1) |
| Pressure | 500–4000 psig | 700–3000 psig |
| Solvents | (2) | (2) |
| Concentrations | | |
| MDA: | 10–95% | 50–90% |
| catalyst: | 0.1–15.0% (3) | 0.2–7% (3) |
| lithium hydroxide promoter | 0.01–2% (4) | 0.1–1% (4) |
| water: | 7–12% | >7–10% |

(1) The "Preferred" temperature depends on the desired trans, trans isomer content of the bis(4-aminocyclohexyl)methane. Lower temperatures give a lower (approximate 16–34% trans, trans) content; increasing the temperature results in a higher (approximate 48% trans, trans) content. In order to obtain a low trans, trans content, temperatures below 130° C. should be used, preferably 80–125° C., and most preferably 110–120° C.
(2) Any solvent miscible with water at the reaction temperature and inert to the reaction conditions is usable. Examples include alcohols (isopropyl alcohol, other low molecular weight alcohols, diols, alkoxyalcohols, etc.) and ethers (dioxane, glymes, tetrahydrofuran, etc.).
(3) Based on weight of catalyst to weight of starting amine.
(4) Based on weight of promoter to weight of starting amine.

While the specific invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A process for the catalytic hydrogenation of an aromatic amine represented by the formula:

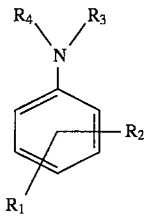

in which:

$R_1$ is selected from the group consisting of H, an alkyl or cycloakyl group having 1–6 carbon atoms, and $NH_2$;

$R_2$ is P-aminobenzyl and $R_3$ and $R_4$ are selected from the group consisting of H, and an alkyl or cycloalkyl group having 1–6 carbon atoms;

which process comprises reacting a reaction mixture comprising said aromatic amine and hydrogen at a pressure of between about 500 and about 4000 psig, and a reaction temperature of below 130° C., in the presence of a ruthenium noble metal catalyst, a lithium hydroxide catalyst promoter, and an aqueous water miscible organic solvent being isopropyl alcohol, said reaction mixture containing water in an amount of between 7% and 12% by weight, based upon the weight of the reaction mixture, to produce a bis(4-aminocyclohexyl)methane product having a trans, trans isomer content of between 16% and 24%.

2. The process of claim 1 in which the water is present in an amount of between 7% and 10% by weight based upon the weight of the reaction mixture.

3. The process of claim 1 in which $R_1$ $R_3$, and $R_4$ are hydrogen.

4. The process of claim 1 in which the lithium hydroxide catalyst promoter is present in a concentration from about 0.01% to about 2% by weight of the aromatic amine.

5. The process of claim 1 in which the lithium hydroxide catalyst promoter is present in a concentration from about 0.1% to about 1% by weight of the aromatic amine.

6. The process of claim 1 wherein said ruthenium noble metal catalyst is on an aluminum support.

7. The process of claim 1 in which said reaction mixture contains water in an amount of between 7.3% and 7.8%, based upon the weight of the reaction mixture.

8. The process of claim 1 in which the reaction is carried out at a temperature in the range from about 80° C. to about 125° C.

9. The process of claim 1 in which the reaction is carried out at a temperature in the range from about 110° C. to about 120° C.

10. The process of claim 6 wherein said catalyst on said support is employed in an amount of between 0.1% and 15.0% based upon the amount of said aromatic amine employed.

11. The process of claim 6 wherein said catalyst on said support is employed in an amount of between 0.2% and 0.7% based upon the amount of said aromatic amine employed.

12. A process for the catalytic hydrogenation of methylenedianiline which comprises reacting a reaction mixture comprising said methylenedianiline and hydrogen at a pressure of between about 500 psig and about 4000 psig, and a reaction temperature of between 80° C. and 170° C. in the presence of a noble metal catalyst, a lithium hydroxide catalyst promoter, and an aqueous water miscible organic solvent comprising isopropyl alcohol, said reaction mixture containing water in an amount of between 7% and 12% by weight, based upon the weight of the reaction mixture, to produce a bis(4-aminocyclohexyl)methane product having a trans, trans isomer content of 20% or less.

* * * * *